United States Patent
Fathman

(10) Patent No.: US 7,378,089 B2
(45) Date of Patent: May 27, 2008

(54) GENE THERAPY FOR THE PREVENTION OF AUTOIMMUNE DISEASE

(75) Inventor: C. Garrison Fathman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1056 days.

(21) Appl. No.: 10/263,937

(22) Filed: Oct. 2, 2002

(65) Prior Publication Data

US 2003/0091548 A1    May 15, 2003

Related U.S. Application Data

(60) Provisional application No. 60/326,668, filed on Oct. 2, 2001.

(51) Int. Cl.
*A01N 63/00* (2006.01)
*A01N 65/00* (2006.01)

(52) U.S. Cl. .................................. 424/93.71

(58) Field of Classification Search .................. None
See application file for complete search history.

(56) References Cited

U.S. PATENT DOCUMENTS 5,958,403 A    9/1999  Strom et al.
6,274,136 B1   8/2001  Weiner et al.

OTHER PUBLICATIONS

Feili-Hariri, M., et al. Diabetes. 1999;48:2300-2308.*
Cameron, M.J., et al. Hum. Gene. Ther. 2000;11:1647-1656.*
Chen et al., A gene therapy approach for treating T cell mediated autoimmune diseases, (2001), Blood, 97: 886-894.
Yasuda et al., Local expression of immunoregulatory IL-12p40 gene prolonged syngeneic islet graft survival in diabetic NOD mice, (1998), J. Clin. Invest., 102: 1807-1814.
Costa et al., (2001), J. Immunol., 167(4): 2379-2387.
Costa et al., (2000), J. Immunol., 164: 3851-3590.
Gallichan et al., (1998), Hum. Gene Ther., 9(18): 2717-2726.
Issazadeh et al., (1995), J. Neuroimmunol, 61:205-12.
Macatonia et al., (1993), Int. Immunol., 5: 1119-28.
Nakajima et al., (2001), The Journal of Clinical Investigation, 107(10): 1293-1301.
Racke et al., (1994), J. Exp. Med., 180: 1961-6.
Shaw et al., (1997), J. Exp. Med., 185(9): 1711-1714.
Smith et al., (1997), Transplantation, 64(7): 1040-1049.
Takayama et al., (2001), Transplantation, 71: 1334-1340.
Voorthuis et al., (1990), Clin. Exp. Immunol., 81: 183-8.
Yamamoto et al., (2001), J. Immunol., 166: 4973-4980.

* cited by examiner

*Primary Examiner*—G. R Ewoldt
(74) *Attorney, Agent, or Firm*—Bozicevic, Field & Francis LLP; Pamela J. Sherwood

(57) ABSTRACT

Autoimmune disease is treated by the delivery of a suppressive agent to the site of disease. Delivery is accomplished by introducing an expression vector encoding the suppressive agent into cells targeted for such sites, and administering the genetically modified cells to the patient. Suppressive agents of particular interest include IL-4; and anti-CD3 antibodies, particularly single chain anti-CD3 antibodies. Cells of interest for delivery include T cells and T cell hybridomas, where the T cell antigen receptor recognizes epitopes associated with the autoimmune disease. Alternatively, dendritic cells are used as delivery vectors.

3 Claims, 4 Drawing Sheets

Day 1 : 1 hour after injectio
NOD

NOD   Day 3, 40 hours after injection pancreas spleen

GENE THERAPY FOR THE PREVENTION OF AUTOIMMUNE DISEASE

INTRODUCTION

The complexity of the immune system has been a daunting barrier to an understanding of immune system dysfunction. Modulation of the immune response varies with the specific factors produced, and the receptors present on the responding cell. The pathways for down-regulating responses are as important as those required for activation. T cell tolerance is one well-known mechanism for preventing an immune response to a particular antigen. Other mechanisms, such as secretion of suppressive cytokines, are also known.

A common feature in a number of diseases and inflammatory conditions is the involvement of pro-inflammatory $CD4^+$ T cells. These T cells are responsible for the release of inflammatory, Th1 type cytokines. Cytokines characterized as Th1 type include interleukin 2 (IL-2), γ-interferon, TNFα and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-β. It has been found that Th1 and Th2 type T cells may use the identical antigen receptor in response to an immunogen; in the former producing a stimulatory response and in the latter a suppressive response.

Cytokines play a critical role in the development and recovery from autoimmune diseases. Th1 cytokines such as interleukin 12 (IL-12) and interferon gamma (IFNγ) have been found in the central nervous system (CNS) of multiple sclerosis (MS) patients as well as in animals with EAE (Issazadeh et al. (1995). *J Neuroimmunol* 61:205-12). Th2 cytokines such as IL-4, IL-5 and IL-10 have been found to be elevated either during remission of MS or EAE (Waisman et al. (1997) Immunointervention in autoimmunity by Th1/Th2 regulation, L. Adorini, ed. (Austin, Tex.: R. G. Landes Co.), pp. 129-50). Previous studies have shown that systemic administration of IL4 as well as local CNS administration of IFNγ can reduce the severity of EAE (Racke et al. (1994) *J Exp Med* 180:1961-6; Voorthuis et al. (1990) *Clin Exp Immunol* 81:183-8). Furthermore, the addition of IL-4 to naive T cells can result in the development of Th2 type cells, whereas the addition of IL-12 can result in the development of Th1 type cells (Macatonia et al. (1993) *Int Immunol* 5:1119-28).

SUMMARY OF THE INVENTION

Autoimmune disease is treated by the delivery of a suppressive agent to the site of disease. Delivery is accomplished by introducing an expression vector encoding the suppressive agent into cells targeted for such sites, and administering the genetically modified cells to the patient. Suppressive agents of particular interest include IL-4; and anti-CD3 antibodies, particularly single chain anti-CD3 antibodies.

Cells of interest for delivery include T cells and T cell hybridomas, where the T cell antigen receptor recognizes epitopes associated with the autoimmune disease, e.g. islet cell epitopes for IDDM, myelin basic protein epitopes for multiple sclerosis, collagen epitopes for rheumatoid arthritis, etc. Alternatively, dendritic cells are used as delivery vectors.

In another embodiment, the expression of IL-4 by targeting cells is directed to islet cells through retrograde transduction at the common duct to the pancreas, through oral vectors. The targeted cells are introduced into a patient, where they then migrate to the disease lesion. The expression of IL-4 down-regulates pro-inflammatory immune responses that cause damage to islet cells. In one embodiment of the invention, the patient suffers from hyperglycemia but not overt IDDM.

DETAILED DESCRIPTION OF THE EMBODIMENTS

Figure 1:
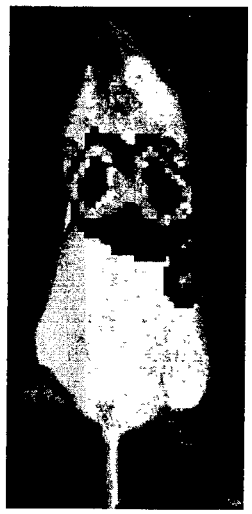
FIG. 1: Bioluminescence imaging one and 40 hours after adoptive transfer of $1 \times 10^6$ 6C5 hybridomas transduced to express luciferase. The animals were anesthetized with an iv anesthetic that contained luciferin. The animals were then imaged for photon emission, using a CCD camera equipped for appropriate data retrieval. The spleen and pancreas were removed and imaged at 40 hours to demonstrate homing of the luciferase expressing 6C5 cells to the pancreas.
Figure 1:
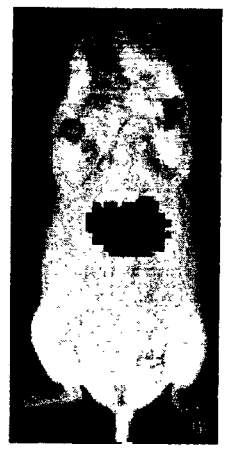
Figure 1:

Suppressive agents are delivered to the site of an autoimmune disease by introducing an expression vector encoding the suppressive agent into cells targeted for such sites, and introducing the cells in the host. In one embodiment of the invention, the targeted cell is a T cell or T cell hybridoma that is specific for an autoantigen. Autoantigen-specific T cells have tissue-specific homing properties, which provides them for the local delivery of immunoregulatory molecules. Autoantigens, as used herein, are endogenous proteins or fragments thereof that elicit a pathogenic immune response. Of particular interest are autoantigens that induce a T cell mediated inflammatory pathogenic responses, such as multiple sclerosis, experimental autoimmune encephalitis, rheumatoid arthritis and insulin dependent diabetes mellitus. In another embodiment, the targeted cell is a dendritic cell. Another route for gene delivery is retrograde transduction, e.g. via the common bile duct through cannulation, endoscopy, etc. In this method, a virus vector comprising coding sequences of a suppressive agent is introduced directly to the patient.

In one embodiment of the invention, the patient is diabetic and suffers from hyperglycemia but not overt IDDM. The cells expressing the suppressive agent are useful in therapy to treat hyperglycemia and to prevent the onset of IDDM; to down-regulate the responsiveness of T cells, etc. Transfer of engineered cells that express IL-4 are shown to significantly inhibit the development of IDDM in patients suffering from hyperglycemia, an early stage of the disease.

The subject methods of targeted immunosuppression are used for prophylactic or therapeutic purposes. Use used herein, the term "treating" is used to refer to both prevention of disease, and treatment of pre-existing conditions. The prevention of autoimmune disease is accomplished by administration of the therapeutic cells prior to development of overt disease. The treatment of ongoing disease, where the therapeutic cells stabilize or improve the clinical symptoms of the patient, is of particular interest. Such treatment is desirably performed prior to complete loss of function in the affected tissues, e.g. during the initial stages when the patient is hyperglycemic but there is not substantial destruction of islet cells. Animal models, particularly small mammals, e.g. murine, lagomorpha, etc. are of interest for experimental investigations.

Suppressive agents

The targeted cells are modified to express the suppressive agents, e.g. IL4 or anti-CD3 antibody. The lymphokine IL-4 has T-cell and mast cell growth factor activities. Human IL4 is an 18-kD glycoprotein (Yokota et al. (1986) *P.N.A.S.* 83:5894-5898). This sequence is the preferred sequence of the invention. However, the invention is not limited to the use of this sequence in constructs of the invention. Also of use are closely related variant sequences that have the same biological activity, or substantially similar biological activity.

OKT3, an antibody specific for the CD3 chain of the TCR complex, has been used clinically for over a decade in the treatment of steroid-resistant graft rejection. Nonmitogenic forms of anti-CD3 have been created by altering binding to Fc receptor. Treatment with the nonmitogenic anti-CD3 results in internalization of the TCR complex and depletion of T cells from the circulation and peripheral lymphoid organs. Anti-CD3-IgG3 does not induce global T cell unresponsiveness. Of particular interest are humanized forms of the antibody, and single chain variants. For example, see Alegre et al. (1995) *J. Immunol.* 155:1544-1555; Hirsch et al. (1988) *J. Immunol.* 140:3766-3772; Herold et al. (2002) *N Engl J Med* 346(22):1692-8.

Variant sequences encode protein subunits which, when present in a DNA construct of the invention, give the protein one or more of the biological properties of IL-4 or anti-CD3. DNA sequences of the invention may differ from a native sequence by the deletion, insertion or substitution of one or more nucleotides, provided that they encode a protein with the appropriate biological activity as described above. Similarly, they may be truncated or extended by one or more nucleotides. Alternatively, DNA sequences suitable for the practice of the invention may be degenerate sequences that encode the naturally occurring protein. Typically, DNA sequences of the invention have at least 70%, at least 80%, at least 90%, at least 95% or at least 99% sequence identity to a native coding sequence. They may originate from any species, though DNAs encoding human proteins are preferred. Variant sequences may be prepared by any suitable means known in the art.

With respect of substitutions, conservative substitutions. are preferred. Typically, conservative substitutions are substitutions in which the substituted amino acid is of a similar nature to the one present in the naturally occurring protein, for example in terms of charge and/or size and/or polarity and/or hydrophobicity. Similarly, conservative substitutions typically have little or no effect on the activity of the protein. Proteins of the invention that differ in sequence from naturally occurring proteins may be engineered to differ in activity from the naturally occurring protein. Such manipulations will typically be carried out at the nucleic acid level using recombinant techniques, as known in the art.

The coding sequence is inserted into an appropriate expression cassette. The expression construct is prepared in conventional ways. The cassette will have the appropriate transcriptional and translational regulatory sequences for expression of the sequence in the targeted cells. The cassette will generally be a part of a vector, which contains a suitable origin of replication, and such genes encoding selectable markers as may be required for growth, amplification and manipulation of the vector, prior to its introduction into the recipient. Suitablevectors include plasmids, YACs, BACs, bacteriophage, retrovirus, and the like. Viral vectors of interest include retrovirus, adenovirus, adeno associated virus, lentivirus, and the like.

The expression cassette will generally employ an exogenous transcriptional initiation region, i.e. a promoter other than the native promoter, which is functional in the targeted cells. The promoter may be introduced by recombinant methods in vitro, or as the result of homologous integration of the sequence by a suitable host cell. The promoter is operably linked to the coding sequence of the coding sequence to produce a translatable mRNA transcript. Expression vectors conveniently will have restriction sites located near the promoter sequence to facilitate the insertion of autoantigen sequences. Many strong promoters for mammalian cells are known in the art, including the β-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

The expression construct may be introduced into targeted T cells, T cell hybridomas or dendritic cells by any number of routes, including viral infection, microinjection, or fusion of vesicles. Jet injection may also be used for intramuscular administration, as described by Furth et al. (1992) *Anal Biochem* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the GRAIL protein or DNA, then bombarded into skin cells.

Dendritic cell

As used herein, the term refers to any member of a diverse population of morphologically similar cell types found in lymphoid or non-lymphoid tissues. Dendritic cells are referred to as "professional" antigen presenting cells, and have a high capacity for sensitizing MHC-restricted T cells. Dendritic cells may be recognized by function, by phenotype and/or by gene expression pattern, particularly by cell surface phenotype. These cells are characterized by their distinctive morphology, high levels of surface MHC-class II expression and ability to present antigen to CD4+ and/or CD8+ T cells, particularly to naïve T cells (Steinman et al. (1991) *Ann. Rev. Immunol.* 9:271; incorporated herein by reference for its description of such cells).

The cell surface of dendritic cells is unusual, with characteristic veil-like projections, and is characterized by expression of the cell surface markers CD11c and MHC class II. Most DCs are negative for markers of other leukocyte lineages, including T cells, B cells, monocytes/macrophages, and granulocytes. Subpopulations of dendritic cells may also express additional markers including 33D1, CCR1, CCR2, CCR4, CCR5, CCR6, CCR7, CD1a-d, CD4, CD5, CD8alpha, CD9, CD11b, CD24, CD40, CD48, CD54, CD58, CD80, CD83, CD86, CD91, CD117, CD123 (IL3Rα), CD134, CD137, CD150, CD153, CD162, CXCR1, CXCR2, CXCR4, DCIR, DC-LAMP, DC-SIGN, DEC205, E-cadherin, Langerin, mannose receptor, MARCO, TLR2, TLR3 TLR4, TLR5, TLR6, TLR9, and several lectins. The patterns of expression of these cell surface markers may vary along with the maturity of the dendritic cells, their tissue of origin, and/or their species of origin.

Immature dendritic cells express low levels of MHC class II, but are capable of endocytosing antigenic proteins and processing them for presentation in a complex with MHC class II molecules. Activated dendritic cells express high levels of MHC class II, ICAM-1 and CD86, and are capable of stimulating the proliferation of naïve allogeneic T cells, e.g. in a mixed leukocyte reaction (MLR).

Functionally, dendritic cells may be identified by any convenient assay for determination of antigen presentation. Such assays may include testing the ability to stimulate antigen-primed and/or naïve T cells by presentation of a test antigen, followed by determination of T cell proliferation, release of IL-2, and the like.

T cells

In one embodiment of the invention, T cells are selected for responsiveness to epitopes related to the development of autoimmune disease. T cells may be isolated from patient peripheral blood, lymph nodes, or preferably from the site of inflammation. Reactivity assays may be performed on primary T cells, or the cells may be fused to generate hybridomas. Such reactive T cells may also be used for further analysis of disease progression, by monitoring their in situ location, T cell receptor utilization, etc. Assays for monitoring T cell responsiveness are known in the art, and include proliferation assays and cytokine release assays. T cells specific for autoantigens may be isolated from a patient, from an allogeneic source, or may be activated in vitro from non-activated T cells, which can be allogeneic, autologous, etc. (see U.S. Pat. No. 5,846,82).

Human cell hybridomas are developed by fusing activated T lymphocytes exhibiting a desired immunological function with an immortal human T cell line with the objective to immortalize the T cell properties of interest (see Fathman et al. (1983) *Annu Rev Immunol* 1:633-655). For example, mutagenized human tumor T cell lines, deficient for the enzyme hypoxanthine-guanine phosphoribosyl transferase have been used for the development of T-T cell hybrids. Unfused tumor cells are removed by using appropriate selection media. Alternatively a T cell line may be chemically treated before the fusion with irreversible biochemical inhibitors to eliminate any unfused cells of the T cell line. Hybrids can also be selected on the basis of their ability to form colonies in soft agar, and their hybrid nature is confirmed by HLA typing and functional tests. As an alternative to hybridomas, T cells can be maintained through the addition of growth factors and/or cells providing antigenic stimulation in order to maintain the cells in culture for a period of time sufficient to introduce the IL-4 coding sequences.

Autoantigens

Autoantigens known to be associated with disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA12); IA-2; IA-2beta; HSP; glima 38; ICA69; and p52 with insulin dependent diabetes. For example, insulin (which sequence is publicly available, for example from Sures et al. (1980) *Science* 208:57-59; Bell et al. (1979) *Nature* 282:525-527; and Bell et al. (1980) *Nature* 284:26-32) has been found to have immunodominant epitopes in the B chain, e.g. residues 9-23; as well as in the pre-proinsulin leader sequence. An association of GAD epitopes with diabetes is described in a number of publications, including U.S. Pat. No. 5,212,447; and European patent application no. 94.927940.0. GAD65 epitopes include residues 206-220; 221-235, 286-300; 456-470; and peptides including residues p247, p509; p524 (Kauffman et al. (1993) Nature 366:69-72). An association of insulin epitopes with autoimmune insulitis is described in Griffin et al. (1995) *Am. J. Pathol.* 147:845-857. Rudy et al. (1995) Mol. Med. 1:625-633 disclose an epitope that is similar in GAD and proinsulin.

The protein components of myelin proteins, including myelin basic protein (MBP), proteolipid protein (PLP), myelin-associated glycoprotein (MAG) and myelin oligodendrocyte glycoprotein (MOG), are of particular interest for use as immunogens of the invention. The suppression of T cell responsiveness to these antigens is used to prevent or treat demyelinating diseases. Proteolipid is a major constituent of myelin, and is known to be involved in demyelinating diseases (see, for example Greer et al. (1992) *J. Immunol.* 149:783-788 and Nicholson (1997) *Proc. Natl. Acad. Sci. USA* 94:9279-9284).

The integral membrane protein PLP is a dominant autoantigen of myelin. Determinants of PLP antigenicity have been identified in several mouse strains, and include residues 139-151 (Tuohy et al. (1989) *J. Immunol.* 142:1523-1527), 103-116 (Tuohy et al. (1988) *J. Immunol.* 141:1126-1130], 215-232 (Endoh et al. (1990) *Int. Arch. Allergy Appl. Immunol.* 92:433-438), 43-64 (Whitham et al. (1991) *J. Immunol.* 147:3803-3808) and 178-191 (Greer, et al. (1992) *J. Immunol.* 149:783-788).

MBP is an extrinsic myelin protein that has been studied extensively. At least 26 MBP epitopes have been reported (Meinl et al. (1993) *J. Clin. Invest.* 92:2633-2643). The immunodominant MBP(84-102) peptide has been found to bind with high affinity to DRB1*1501 and DRB5*0101 molecules of the disease-associated DR2 haplotype. Overlapping but distinct peptide segments were important for binding to these molecules; hydrophobic residues (Val189 and Phe92) in the MBP (88-95) segment for peptide binding to DRB1*1501 molecules; hydrophobic and charged residues (Phe92, Lys93) in the MBP (89-101/102) sequence contributed to DRB5*0101 binding.

The transmembrane glycoprotein MOG is a minor component of myelin that has been shown to induce EAE. Immunodominant MOG epitopes that have been identified in several mouse strains include residues 1-22, 35-55, 64-96 (deRosbo et al. (1998) J. Autoimmunity 11:287-299, deRosbo et al. (1995) Eur J Immunol. 25:985-993) and 41-60 (Leadbetter et al. (1998) J Immunol 161:504-512).

Autoantigens associated with rheumatoid arthritis may comprise epitopes from type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; cardiolipin; aldolase A; citrulline-modified filaggrin and fibrin, etc. Autoantibodies that recognize filaggrin peptides containing a modified arginine residue (deiminated to form citrulline) have been identified in the serum of a high proportion of RA patients.

Antigen panels or arrays for myasthenia gravis may include epitopes with the acetylcholine receptor. For Grave's disease epitopes may include the Na+/I– symporter; thyrotropin receptor; Tg; and TPO. Sjogren's syndrome panels may include SSA (Ro); SSB (La); and fodrin. Panels for pemphigus vulgaris may include desmoglein-3. Panels for myositis may include tRNA synthetases (e.g., threonyl, histidyl, alanyl, isoleucyl, and glycyl); Ku; PM/ScI; SSA; U1 sn-ribonuclear protein; Mi-1; Mi-1; Jo-1; Ku; and SRP. Panels for scleroderma may include ScI-70; centromere proteins; U1 ribonuclear proteins; and fibrillarin. Panels for primary biliary cirrhosis may include pyruvate dehydrogenase E2 and alpha-ketoglutarate dehydrogenase components. Panels for pernicious anemia may include intrinsic factor; and glycoprotein beta subunit of gastric H/K ATPase.

Diseases of Interest

Human insulin-dependent diabetes mellitus (IDDM) is a disease characterized by autoimmune destruction of the β cells in the pancreatic islets of Langerhans. An animal model for the disease is the non-obese diabetic (NOD) mouse, which develops autoimmunity. NOD mice spontaneously develop inflammation of the islets and destruction of the β cells, which leads to hyperglycemia and overt diabetes. Both CD4+ and CD8+ T cells are required for diabetes to develop: CD4+ T cells appear to be required for initiation of insulitis, cytokine-mediated destruction of β cells, and probably for activation of CD8+ T cells. The CD8+ T cells in turn mediate β cell destruction by cytotoxic effects such as release of granzymes, perforin, TNFα and IFNγ. Reactivity to several candidate autoantigens, including epitopes of insulin and glutamic acid decarboxylase (GAD), have been detected.

The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic β cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) *Nature Genetics* 9:293-298).

Markers that may be evaluated during the presymptomatic stage are the presence of insulitis in the pancreas, the level and frequency of islet cell antibodies, islet cell surface antibodies, aberrant expression of Class II MHC molecules on pancreatic β cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual b cell function, evidenced by the plasma persistence of insulin C-peptide, may also benefit from the subject treatment, to prevent further loss of function.

The subject therapy will desirably be administered during the presymptomatic or preclinical stage of the disease, and in some cases during the symptomatic stage of the disease. Early treatment is preferable, in order to prevent the loss of function associated with inflammatory tissue damage. The presymptomatic, or preclinical stage will be defined as that period not later than when there is T cell involvement at the site of disease, e.g. islets of Langerhans, synovial tissue, thyroid gland, etc., but the loss of function is not yet severe enough to produce the clinical symptoms indicative of overt disease. T cell involvement may be evidenced by the presence of elevated numbers of T cells at the site of disease, the presence of T cells specific for autoantigens, the release of performs and granzymes at the site of disease, response to immunosuppressive therapy, etc.

Degenerative joint diseases may be inflammatory, as with seronegative spondylarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous collagens are attacked by metalloproteases, and when the collagenous microskeleton is lost, repair by regeneration is impossible.

There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional NSAID treatment. Generally, the subject treatment will not be combined with such disease modifying drugs as cyclosporin A, methotrexate, and the like.

A quantitative increase in myelin autoreactive T cells with the capacity to secrete IFN-gamma is associated with the pathogenesis of MS and EAE, suggesting that autoimmune, inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Mammalian species susceptible to inflammatory conditions include canines and felines; equines; bovines; ovines; etc. and primates, particularly humans. Animal models, particularly small mammals, e.g. murine, lagomorpha, etc. may be used for experimental investigations. Animal models of interest include those involved with the production of antibodies having isotypes associated with IL-4 production, e.g. IgE, IgG1 and IgG4. Other uses include investigations where it is desirable to investigate a specific effect in the absence of T cell mediated inflammation.

The genetically modified cells may be used for the treatment of disease in a recipient. Autologous cells or allogeneic cells may be used. The cells may be administered in any physiologically acceptable medium, normally intravascularly, although they may also be introduced into the targeted site, where the cells home to the site of inflammation. Usually, at least $1 \times 10^5$ cells will be administered, preferably $1'10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors, and the like. The cells localize at the site of lesions, where there is increased inflammation related to the relevant autoantigen. Lesions sites for IDDM are the pancreas; for demyelinating diseases lesion sites are primarily in the central nervous system; for arthritis the joints are primary sites of lesions.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

CD4+ T lymphocytes have been demonstrated to infiltrate the islets of Langerhans as early as day 14 (the earliest date at which PCR reactions of islet tissue amplify TCR products). Multiple T cell hybridomas were generated from islet infiltrating cells from several separate groups of 14-day-old NOD mice. Studies using luciferase transduced cells and luciferin bioluminescence, demonstrated that these hybridomas, rapidly and preferentially homed to the pancreas of NOD mice (FIG. 1). As described in studies below, one of these hybridomas, and the well-characterized BDC2.5 hybridoma, were transduced with retroviral vectors to drive expression of various "regulatory proteins" to deliver these immunoregulatory proteins to the inflamed islets of pre-diabetic cytoxan treated NOD male mice. Therapy of cytoxan treated NOD male mice with T cell transductants expressing IL-4 was effective in preventing the onset of hyperglycemia, when compared to IL-12p40 transductants or control vector-transduced hybridomas (Table 1).

TABLE 1

Incidence of Diabetes in male NOD mice that received IL-4 or IL-12p40 secreting CD4+T cell hybridomas 48 hours following treatment with the second course of ip cytoxan: (200 mg/kg given at day 0 and 14).

|  | No Rx | pGCy | pGCy.IL-4 | pGCy.IL-12p40 |
|---|---|---|---|---|
| BDC2.5 hybridomas |  |  |  |  |
| Exp 11 ($3 \times 10^6$) | 8/10 | 7/10 | 2/10 | 8/10 |
| Exp 11b ($1 \times 10^6$) | 4/5 | ND | 0/5 | ND |
| Exp 20 ($5 \times 10^6$) | 3/5 | 5/5 | 2/8 | 6/10 |
| Exp 21 ($3 \times 10^6$) | ND | 6/10 | ND | 5/10 |
| 6C5 hybridomas |  |  |  |  |
| Exp 22 ($1 \times 10^6$) | 4/6 | 4/7 | 1/7 | ND |
| Exp 24 ($1 \times 10^6$) | ND | 7/10 | 1/10 | 6/10 |

Figure 2:
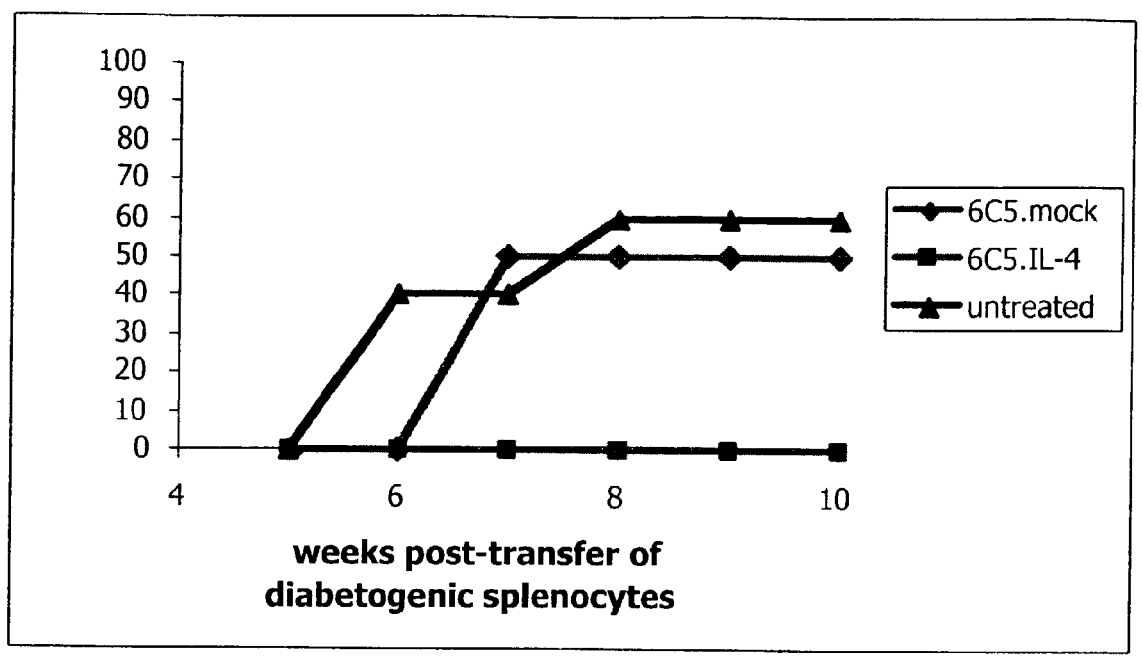
FIG. 2. $15 \times 10^6$ spleen cells from overtly diabetic mice co-transferred into NOD.SCID mice along with $5 \times 10^5$ 6C5 hybridoma cells transduced to express IL-4, were effective in blocking the adoptive transfer of IDDM when compared to vector transduced cells, or non-transduced cells

We were also able to demonstrate that the IL-4 expressing 6C5 transductants blocked progression to overt diabetes in a co-adoptive transfer model of IDDM. In these studies, $15 \times 10^6$ spleen cells from overtly diabetic mice co-transferred into NOD.SCID mice along with $5 \times 10^5$ 6C5 hybridoma cells transduced to express IL-4, were effective in blocking the adoptive transfer of IDDM when compared to vector transduced cells, or non-transduced cells (FIG. 2). The data presented in FIG. 2 and Table 1 demonstrate that local delivery of IL-4 has a protective role in preventing islet inflammation and subsequent IDDM.

Figure 3A:
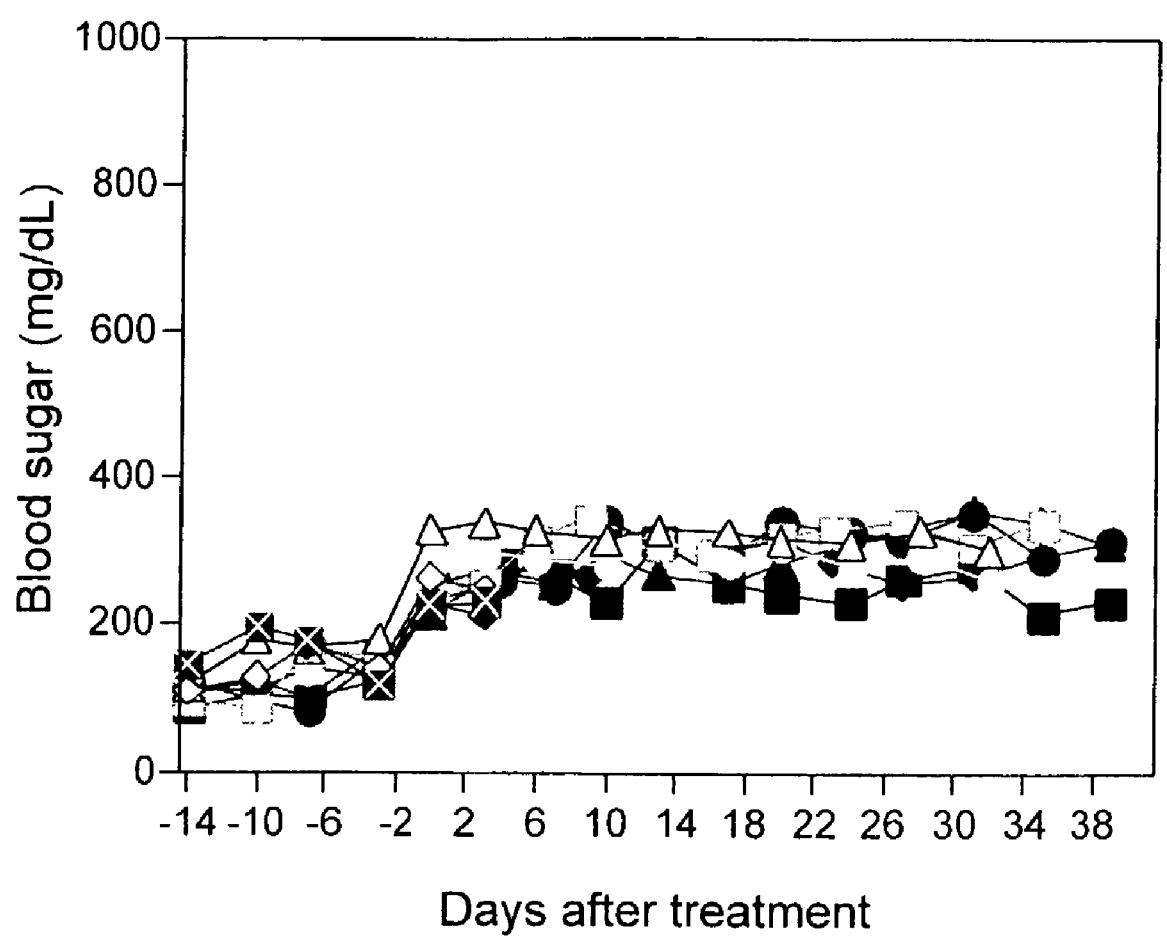
FIG. 3A: Blood sugar levels in spontaneously hyperglycemic ~15 week old NOD mice following treatment (at day zero), with islet antigen specific T cell hybridomas retrovirally transduced to secrete IL-4.
Figure 3B:
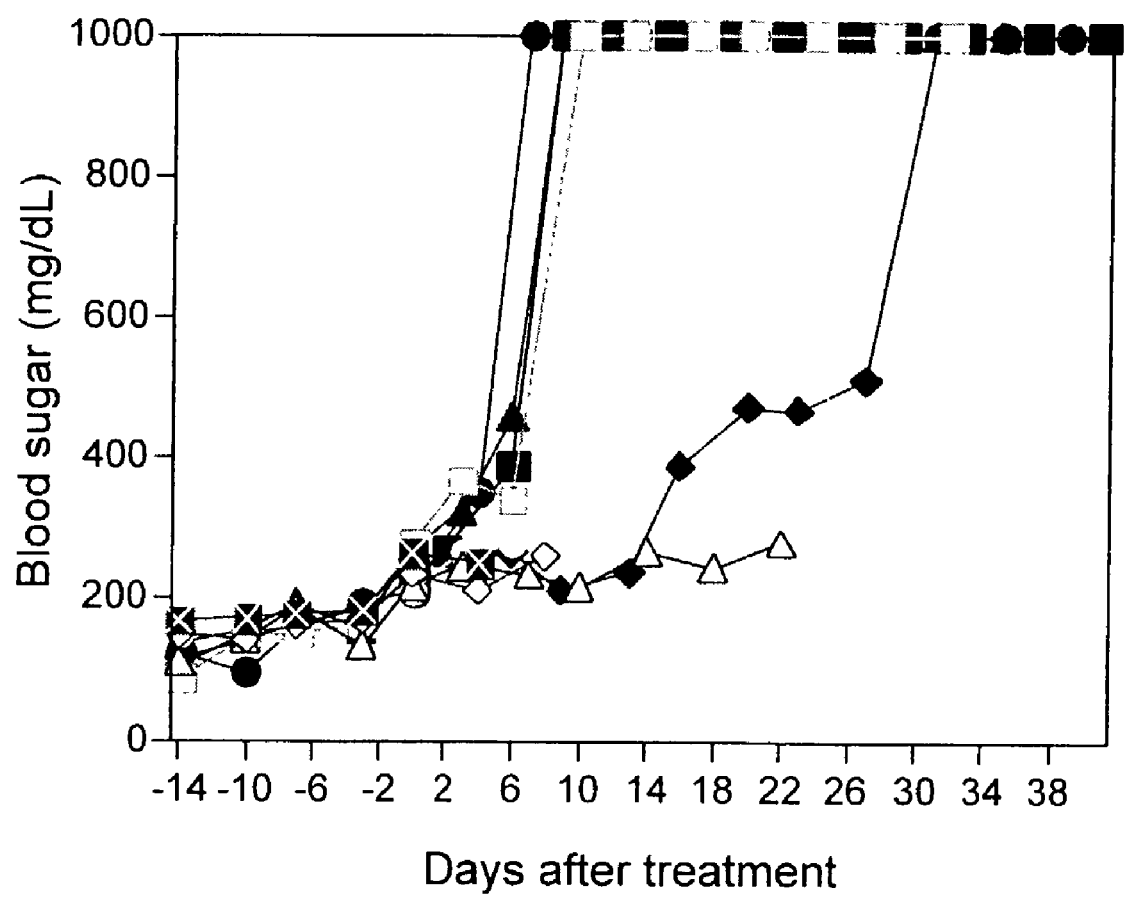
FIG. 3B: Blood sugar levels in spontaneously hyperglycemic ~15 week old NOD mice following treatment (at day zero), with islet antigen specific T cell hybridomas retrovirally transduced with vector control.

Following these observations, 6C5 T cell hybridomas cells, transduced to express IL-4, or vector controls, were used to treat conventional NOD female mice that had developed recent onset hyperglycemia, in order to demonstrate that cytoxan treated mice were "similar" to recent onset hyperglycemic NOD mice and that any effective treatment of cytoxan induced IDDM might be used to treat NOD mice to arrest or reverse hyperglycemia that precedes insulin dependence. In two independent preliminary studies, female NOD mice that had spontaneously developed hyperglycemia were maintained in a quasi-normoglycemic non-insulin requiring'state for over 4 months (to date) following treatment with 6C5 hybridomas transduced to express IL4, compared to the steady progression to overt diabetes in the vector treated controls (FIG. 3).

Recent data suggest that autologous dendritic cells (DCs) also can be transduced and home to sites of inflammation. In an animal model of CIA the dendritic cells, transduced to express regulatory proteins, were as efficient as transduced collagen reactive T cells at providing therapy of CIA. In trials of autologous DCs transduced to express IL-4 in NOD mice, the findings are supportive that DCs transduced to express IL-4 will prevent progression of early onset hyperglycemia in female NOD mice.

What is claimed is:

1. A method for treating autoimmune disease in a patient, the method comprising:

introducing into said patient a dendritic cell that localizes at the site of autoimmune lesions, wherein said dendritic cell is genetically modified to express an IL-4 encoding genetic sequence;

wherein said dendritic cell localizes at said site of autoimmune lesion and produces said IL-4, thereby treating said autoimmune disease.

2. The method according to claim 1, wherein said autoimmune disease is insulin dependent diabetes mellitus.

3. The method according to claim 1, wherein said autoimmune disease is the progression from hyperglycemia to diabetes in a patient.

* * * * *

UNITED STATES PATENT AND TRADEMARK OFFICE
CERTIFICATE OF CORRECTION

PATENT NO. : 7,378,089 B2
APPLICATION NO. : 10/263937
DATED : May 27, 2008
INVENTOR(S) : Fathman Page 1 of 1

It is certified that error appears in the above-identified patent and that said Letters Patent is hereby corrected as shown below:

Col. 1, line 3, insert as follows:

-- FEDERALLY-SPONSORED RESEARCH OR DEVELOPMENT

This invention was made with Government support under contracts DK039959 and AI039646 awarded by the National Institutes of Health. The Government has certain rights in this invention. --

Signed and Sealed this
Second Day of August, 2011

David J. Kappos
*Director of the United States Patent and Trademark Office*